(12) United States Patent
Douglas et al.

(10) Patent No.: US 11,571,177 B1
(45) Date of Patent: Feb. 7, 2023

(54) METHOD AND APPARATUS FOR IMPROVED MEDICAL IMAGING

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

( * ) Notice: Subject to any disclaimer, the term of this patent is extended or adjusted under 35 U.S.C. 154(b) by 0 days.

(21) Appl. No.: 16/990,154

(22) Filed: Aug. 11, 2020

Related U.S. Application Data

(63) Continuation-in-part of application No. 16/936,293, filed on Jul. 22, 2020, now Pat. No. 11,442,538, and a continuation-in-part of application No. 16/927,886, filed on Jul. 13, 2020, now Pat. No. 11,475,625, and a continuation-in-part of application No. 16/879,758, filed on May 21, 2020, now Pat. No. 10,776,989, and a continuation-in-part of application No. 16/842,631, filed on Apr. 7, 2020, now Pat. No. 11,003,342, and a continuation-in-part of application No. 16/683,256, filed on Nov. 13, 2019, now Pat. No. 11,158,045, and (Continued)

(51) Int. Cl.
*G06T 5/50* (2006.01)
*G06F 3/01* (2006.01)
*G06T 7/00* (2017.01)
*A61B 6/00* (2006.01)
*A61B 6/06* (2006.01)

(52) U.S. Cl.
CPC ............. *A61B 6/5258* (2013.01); *A61B 6/06* (2013.01); *A61B 6/4007* (2013.01); *A61B 6/5235* (2013.01); *A61B 6/545* (2013.01);
*G06F 3/013* (2013.01); *G06T 5/50* (2013.01); *G06T 7/0012* (2013.01); *A61B 6/5264* (2013.01); *G06T 2207/10064* (2013.01); *G06T 2207/10116* (2013.01); *G06T 2207/20221* (2013.01); *G06T 2207/30004* (2013.01)

(58) Field of Classification Search
CPC . G06T 2207/10072; G06T 2207/10081; G06T 2207/10116
See application file for complete search history.

(56) References Cited

U.S. PATENT DOCUMENTS 3,949,229 A * 4/1976 Albert ................. A61B 6/4028
378/143
9,820,709 B2 * 11/2017 Melman ............... A61B 6/5205
(Continued)

OTHER PUBLICATIONS

Neculaes et al., "Multisource X-Ray and CT: Lessons Learned and Future Outlook," Oct. 17, 2014, Digital Object Identifier 10.1109/ACCESS.2014.2363949. (Year: 2014).*

(Continued)

*Primary Examiner* — Ross Varndell

(57) ABSTRACT

This invention provides a method to optimize an x-ray beam for more than one structure within the field of view. The preferred embodiment comprises a modular construction of a collimator comprising multiple materials of varying thickness. A first attenuation is performed by the first portion of the collimator to optimize a first anatomic feature and a second attenuation is performed by the second portion of the collimator to optimize a second anatomic feature.

19 Claims, 10 Drawing Sheets

Related U.S. Application Data a continuation-in-part of application No. 16/594,139, filed on Oct. 7, 2019, now Pat. No. 10,893,844.

(60) Provisional application No. 62/985,363, filed on Mar. 5, 2020.

(56) References Cited

U.S. PATENT DOCUMENTS

| | | | | |
|---|---|---|---|---|
| 2013/0195338 A1* | 8/2013 | Xu | ............... | A61B 6/547 |
| | | | | 382/131 |
| 2020/0160972 A1* | 5/2020 | Beriault | ............. | G06T 7/246 |

OTHER PUBLICATIONS

Ayyangar et al., "Monte Carlo simulation of a multi-leaf collimator design for telecobalt machine using BEAMnrc code," Aug. 28, 2009, DOI: 10.4103/0971-6203.58780 (Year: 2009).*

* cited by examiner

Determine which anatomic structures (e.g., vasculature) are needed to be optimized within the field of view
500

Determine the collimator setting (e.g., number of layers, type of materials, position of each collimator layer) for each anatomic structure within the field of view
501

Position the collimator setting (e.g., number of layers, type of materials, position of each collimator layer) for each anatomic structure within the field of view
502

Generate x-rays
503

Adjust collimation beam
504

Figure 5

Obtain a low dose x-ray to determine the type and thickness of the materials within the field of view.
600

- Determine the x-ray settings (kVp, mA, sec) and collimator settings for a first structure within the field of view.
- Determine the x-ray settings (kVp, mA, sec) and collimator settings for at least one additional structure within the field of view.
601

Perform a first image with the the x-ray settings (kVp, mA, sec) and collimator settings for the first structure within the field of view.
602

Perform at least one additional image with the the x-ray settings (kVp, mA, sec) and collimator settings for the at least one additional structure within the field of view.
603

Fuse images
604

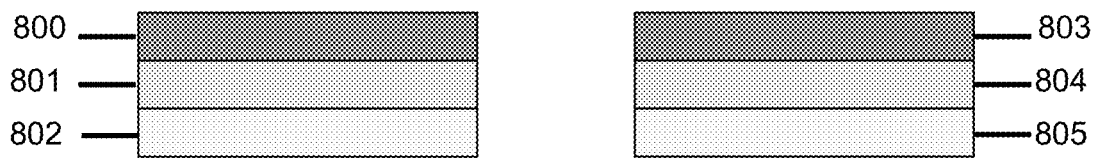

Fig. 8B

| Design Features |
|---|
| • Variable collimator thickness (thickness can vary)<br>• Variable material (e.g., metals such as lead, steel, aluminum or non-lead materials, such as water, plastics, etc.)<br>• Variable direction of placement (front, back, left right)<br>• Variable speed (hollow, disk shaped collimator could be placed)<br>• Variable shape of openings<br>    • e.g., opening conforms to liver<br>    • e.g., preventing radiation from contacting eyes, genitals, etc.<br>• Integration with artificial intelligence<br>• Integration with eye tracking system<br>• Curved detector |

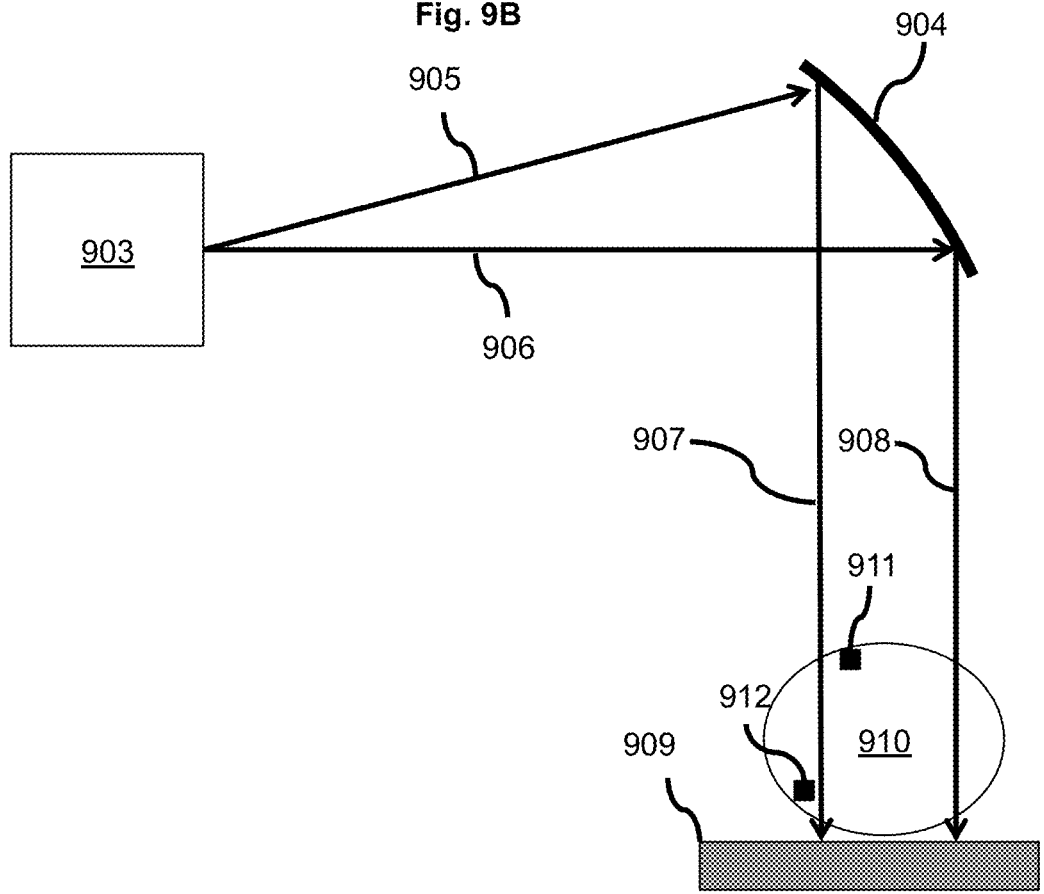

METHOD AND APPARATUS FOR IMPROVED MEDICAL IMAGING

CROSS REFERENCES TO RELATED APPLICATIONS

This patent application is a continuation-in-part of U.S. patent application Ser. No. 16/927,886 filed on Jul. 13, 2020, and U.S. patent application Ser. No. 16/936,293 filed on Jul. 22, 2020, patent application Ser. No. 16/879,758 filed on May 21, 2020 and U.S. patent application Ser. No. 16/842,631 filed on Apr. 7, 2020. In addition, this Patent Application claims the benefit of U.S. Provisional Patent Application 62/856,185 filed on Jun. 3, 2019, U.S. Provisional Patent Application 62/985,363 filed on Mar. 5, 1920 and U.S. Provisional Patent Application 62/939,685 filed on Nov. 25, 2019.

TECHNICAL FIELD

Aspects of this disclosure are generally related to the performance of collimation.

INTRODUCTION

Fluoroscopy can be performed for high spatial resolution and high temporal resolution imaging, such as the vascular system.

SUMMARY

All examples, aspects and features mentioned in this document can be combined in any technically conceivable way.

This invention improves upon the prior art by improving both image quality and reducing patient dose. Specifically, the invention provides a first beam quality to a first region of the image so that the first region of the image is optimized and a second beam quality to a second region of the image so that the second region of the image is optimized.

The preferred embodiment to achieve this inventive step is an apparatus of advanced collimator apparatus with several features. First, the collimator apparatus is designed with multiple layers. Each layer can vary in both thickness and material property. The collimator apparatus is built with a modular design, so that advanced shapes can be obtained, so as to match the shape of a segmented structure within the human body. The collimator apparatus can move in and out at a rapid speed so as to adjust collimation fast enough for both fluoroscopy and to overcome any potential motion artifact from patient movement. The collimator apparatus is integrated into an artificial intelligence system and an eye tracking system.

An alternative apparatus disclosed herein comprises at least two x-ray tubes, which work in synchrony with a large field of view detector. The large field of view detector can be flat (planar) or curved (non-planar). Further, the units can be used in synchrony with a first set of settings (e.g., kVp and mAs) for the first x-ray tube and a second set of settings for the second x-ray tube wherein the first set of settings are different from the second set of settings.

An alternative apparatus disclosed herein comprises an x-ray tube, a system which redirects diverging x-ray photons into a parallel fashion so that parallel x-rays reach the detector in an orthogonal fashion. This eliminates magnification error in radiography and fluoroscopy and is therefore useful.

The large field of view fluoroscopy unit would be performed in the trauma bay or possibly the operating room. A large field of view can include whole body fluoroscopy or radiography.

A method of improving image quality is disclosed. The steps include: determining a first set of x-ray settings that would optimize contrast of a first set of anatomic structures; determining a second set of x-ray settings that would optimize contrast of a second set of anatomic structures; performing a first x-ray image of the first set of anatomic structures; performing a second x-ray image of the second set of anatomic structures; and fusing the first x-ray image of the first set of anatomic structures and the second x-ray image of the second set of anatomic structures to generate an optimized image.

Some embodiments comprise utilizing a first x-ray tube produces the x-rays for the first x-ray image and a second x-ray tube produces the x-rays for the second x-ray image. Some embodiments comprise wherein the first x-ray tube produces an x-ray beam with a wider field of view than an x-ray beam produced by the second x-ray tube.

Some embodiments comprise wherein the first x-ray beam and the second x-ray beam overlap on a detector. Some embodiments comprise utilizing a collimator apparatus wherein the collimator apparatus has a first configuration to cause a first modification of the x-rays generated from an x-ray tube during the first x-ray image and a second configuration to cause a second modification of the x-rays generated from the x-ray tube during the second x-ray image. Some embodiments comprise wherein the collimator apparatus comprises at least two types of materials. Some embodiments comprise wherein the collimator apparatus comprises at least two levels of thickness. Some embodiments comprise wherein the collimator apparatus adjusts its position based on eye tracking data. This is further described in U.S. patent Ser. No. 16/936,293, IMPROVING VISUALIZATION OF IMAGES VIA AN ENHANCED EYE TRACKING SYSTEM, which is incorporated by reference. Some embodiments comprise wherein the collimator apparatus adjusts its position based on inputs from an artificial intelligence system. This is further described in PCT/US2019/023968, RADIOLOGIST ASSISTED MACHINE LEARNING, which is incorporated by reference. Some embodiments comprise wherein the collimator apparatus has a modular construction to be able to form complex shapes to match that of a segmented structure within a patient. Some embodiments comprise wherein the first x-ray image is taken at a first time point and the second x-ray image is taken at a second time point. Some embodiments comprise wherein the first set of x-ray settings comprising mA during the first x-ray image is different from the second set of x-ray settings comprising mA during the second x-ray image. Some embodiments comprise wherein the first set of x-ray settings comprising mAs during the first x-ray image is different from the second set of x-ray settings comprising mAs during the second x-ray image. Some embodiments comprise wherein the first set of x-ray settings comprising kVp during the first x-ray image is different from the second set of x-ray settings comprising kVp during the second x-ray image.

Some embodiments comprise redirecting diverging x-ray photons into a parallel fashion to reach a detector in an orthogonal fashion. This is further described in U.S. Pat. No. 10,346,640 METHOD AND APPARATUS FOR IMPROVEMENT OF SPATIAL RESOLUTION IN MOLECULAR AND RADIOLOGICAL IMAGING, which is incorporated by reference.

Some embodiments comprise a flat panel detector. Some embodiments comprise a curved detector. Some embodiments comprise wherein the flat panel detector a measures at least 50 cm in at least one dimension. Some embodiments comprise performing fluoroscopic images. Some embodiments comprise the steps of: determining at least one additional set of x-ray settings that would optimize contrast of at least one additional set of anatomic structures; and performing the at least one additional x-ray image of at the least one additional set of anatomic structures; and fusing the at least one additional x-ray image to the optimized image.

BRIEF DESCRIPTION OF THE FIGURES

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 illustrates a process for performing an optimized x-ray beam.

FIG. 6 illustrates a process for performing an x-ray beam optimized for more than one structure within the field of view.

FIG. 8A illustrates a collimator made of three different materials.

FIG. 8B illustrates a chart showing various collimator design features.

FIG. 9A illustrates a process wherein the x-ray photons travel towards the detector in a parallel fashion and reach the detector in an orthogonal manner.

FIG. 9B illustrates an apparatus to achieve the process as described in FIG. 9A.

DETAILED DESCRIPTIONS OF THE FIGURES

Figure 1:
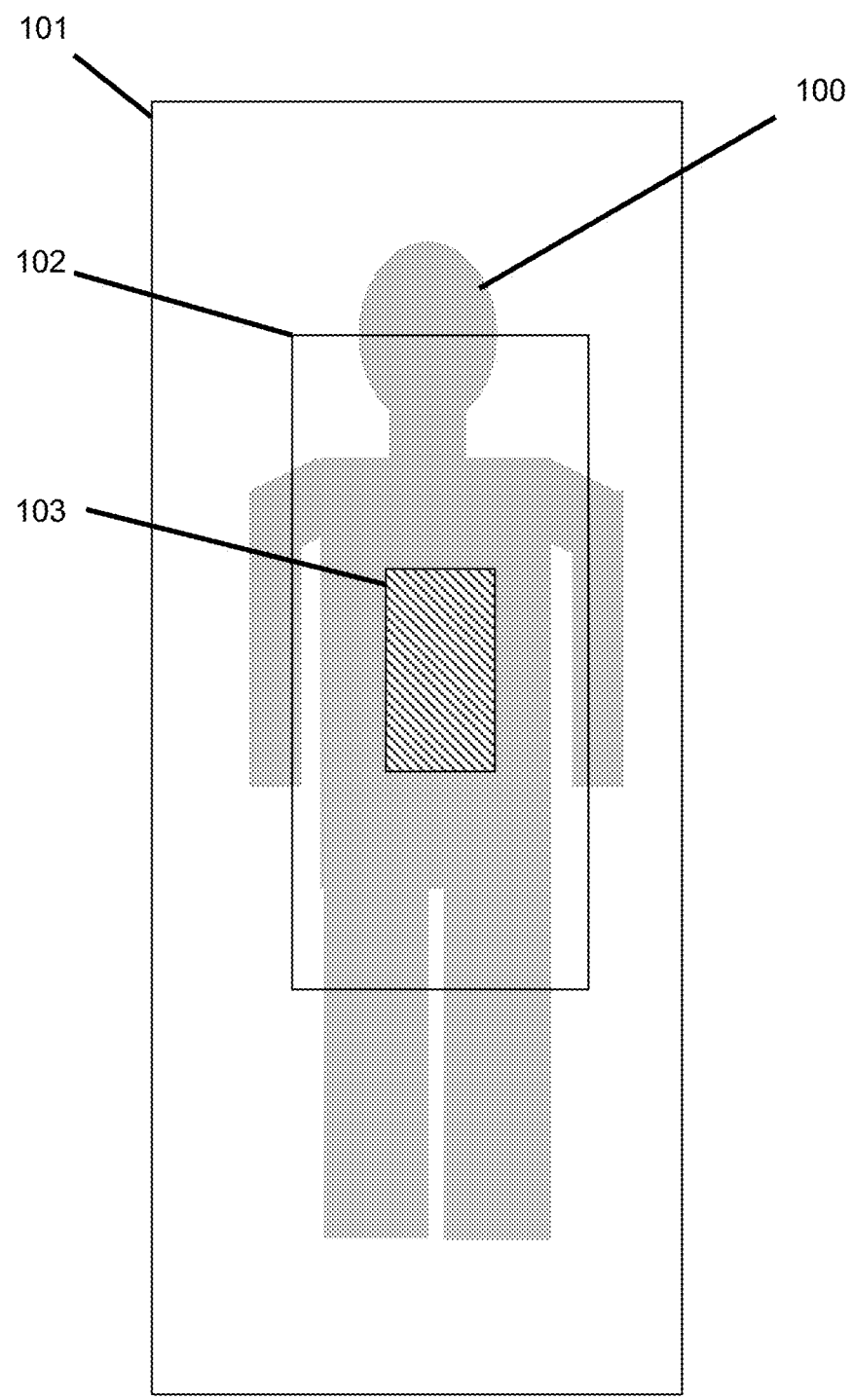
FIG. 1 illustrates the field of view from the first set of photons and the field of view from the second set of photons.

FIG. 1 illustrates the field of view from the first set of photons and the field of view from the second set of photons. 100 illustrates the patient. 101 illustrates the gurney. 102 illustrates the first field of view from the first set of photons, which is large (covering the entirety of the torso of the patient 100). In the preferred embodiment, this would be lower dose (as compared to the second set of photons). This field of view may arise from one or more x-ray tubes. 103 illustrates the second field of view from the second set of photons, which is small (covering only a portion of the torso of the patient 100). In the preferred embodiment, this would be higher dose (as compared to the first set of photons). This field of view may arise from one or more x-ray tubes. Note that the x-ray tubes used for the first field of view 102 and the second field of tube 103 can be from either the same or different x-ray tubes. For example, a single x-ray tube can be used and a first portion of it with a first amount of attenuation to cause the first field of view, which is low dose and a second portion of it with a second amount of attenuation to cause the second field of view, which is higher dose. Note that in this embodiment, the first amount of attenuation is different from the second amount of attenuation. In some embodiments, two x-ray tubes are utilized. The first x-ray tube is set (mA, kVp, etc.) optimized for a large field of view. The second x-ray tube is set (mA, kVp, etc.) optimized for a smaller field of view with improved contrast resolution due to its higher dose. Note that one embodiment is for the x-ray tube(s) to be able to change position and angle, so as to optimize image quality. This setup could be used in the trauma bay. For example, a trauma surgeon could inject contrast into the venous structure and do a run on the entire body at the same time. During this run, the trauma surgeon could assess for both arterial injuries and venous injuries. For example, a trauma surgeon could inject contrast into through a vein in the leg. Fluoroscopic images could be acquired during the venous run and they trauma surgeon could detect venous injuries in the torso (e.g., inferior vena cava injury). The trauma surgeon could continue the fluoroscopic images and then watch the contrast in the arterial phase and then detect any arterial injuries (e.g., renal artery injury). During the initial moments of trauma, it is not known where exactly the sites of bleeding are coming from. Therefore, this rapid whole body fluoroscopy image is useful for diagnostic purposes. In addition, this could be used to strategically place catheters for venous or arterial hemorrhage control devices.

Figure 2:
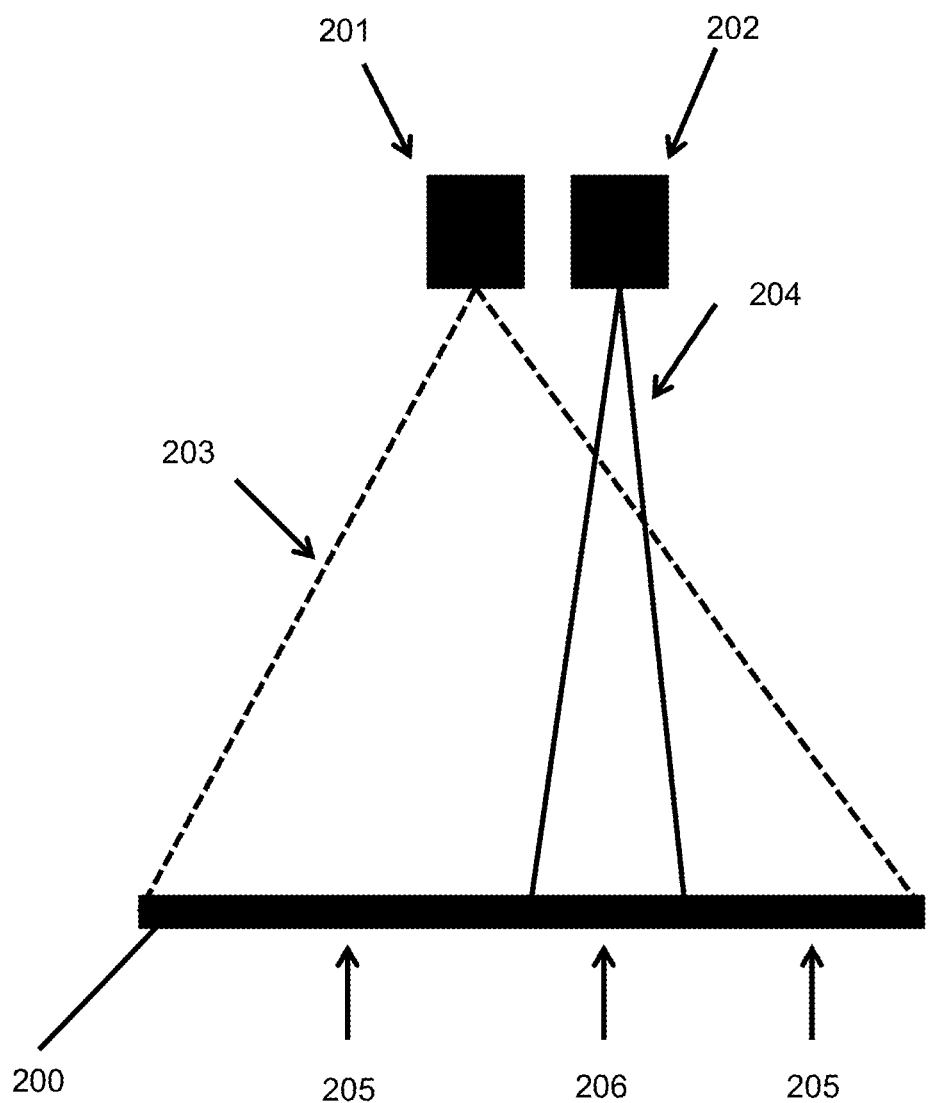
FIG. 2 illustrates a two x-ray tube and single x-ray detector setup.

FIG. 2 illustrates a two x-ray tube and single x-ray detector setup. 200 illustrates the x-ray detector/table setup. 201 illustrates the first x-ray tube. 202 illustrates the second x-ray tube. 203 illustrates the first field of view from the first x-ray tube 201, which is wide. 204 illustrates the second field of view from the second x-ray tube 202, which is narrow. 205 illustrates the portions of the detector covered only by the first x-ray tube 201 and associated first field of view 203. 206 illustrates the portions of the detector covered by both the first x-ray tube 201 and associated first field of view 203 and the second x-ray tube 202 and associated second field of view 204. In some embodiments, the first x-ray tube and the second x-ray tube are on at the same time. In some embodiments, the first x-ray tube and the second x-ray tube are on at different times. In some embodiments, the first x-ray tube and second x-ray tube are performs images at different rates (e.g., first x-ray tube performs images at a 4 frames per second and the second x-ray tube performs images at 16 frames per second). Note the preferred embodiment is a flat panel detector, which measures at least 50 cm in at least one dimension. An alternative embodiment is a flat panel detector, which measures at least 60 cm in at least one dimension. An alternative embodiment is a flat panel detector, which measures at least 70 cm in at least one dimension. An alternative embodiment is a flat panel detector, which measures at least 80 cm in at least one dimension. An alternative embodiment is a flat panel detector, which measures at least 90 cm in at least one dimension. An alternative embodiment is a flat panel detector, which measures at least 100 cm in at least one dimension. An alternative embodiment is a flat panel detector, which measures at least 110 cm in at least one dimension. An alternative embodiment is a flat panel detector, which measures at least 120 cm in at least one dimension. An alternative embodiment is a flat panel detector, which measures at least 130 cm in at least one dimension. An alternative embodiment is a flat panel detector, which measures at least 140 cm in at least one dimension. An alternative embodiment is a flat panel detector, which measures at least 150 cm in at least one dimension. An alternative embodiment is a flat panel detector, which measures at least 160 cm in at least one dimension. An alternative embodiment is a flat panel detector, which measures at least 170 cm in at least one dimension. An alternative embodiment is a flat panel detector, which measures at least 180 cm in at least one dimension. An alternative embodiment is a flat panel detector, which measures at least 190 cm in at least one dimension. An alternative embodiment is a flat panel detector, which measures at least 200 cm in at least one dimension.

Figure 3:
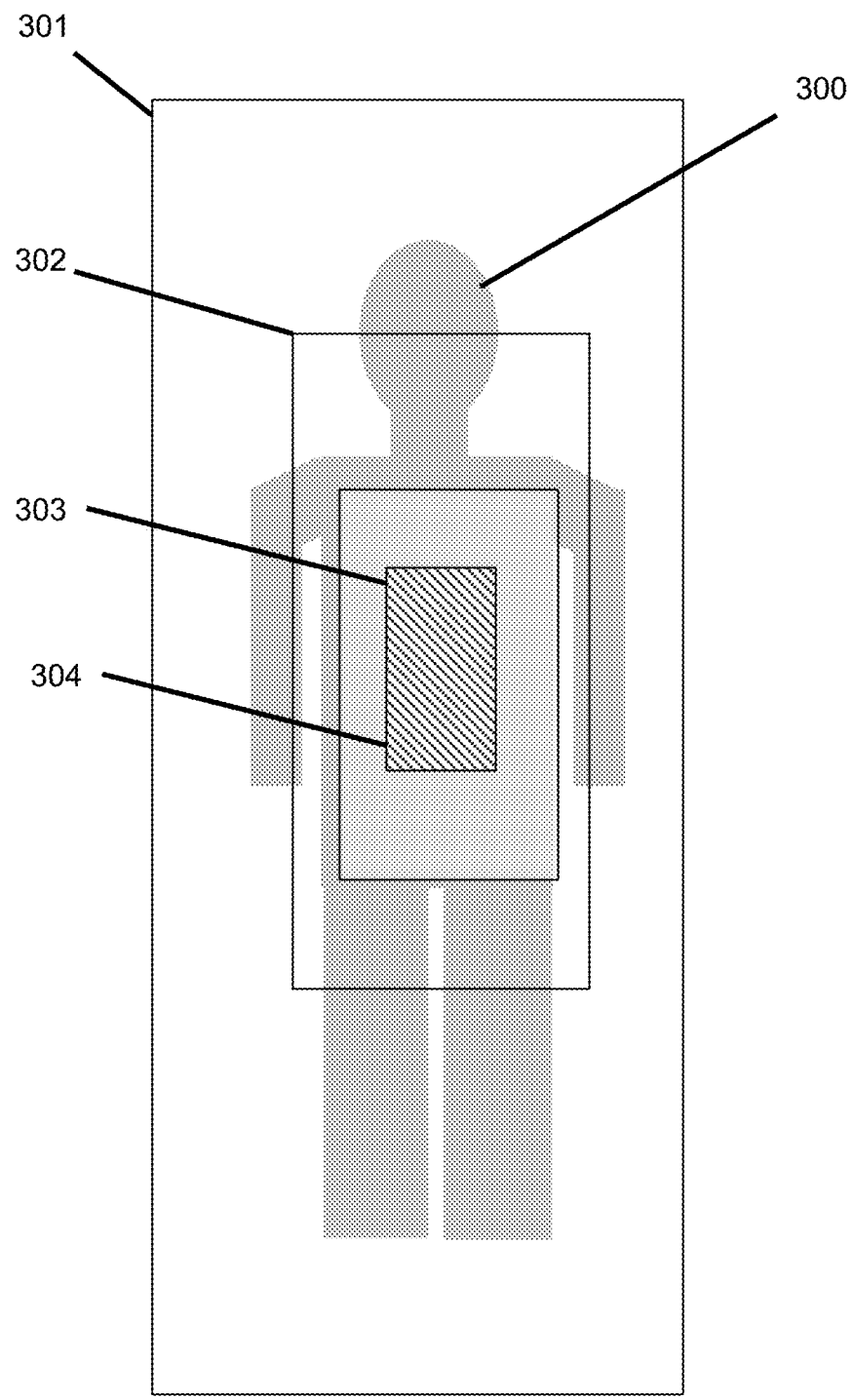
FIG. 3 illustrates a multiple fields of view with variable x-ray beam properties.

FIG. 3 illustrates a multiple fields of view with variable x-ray beam properties. 300 illustrates the patient. 301 illustrates the gurney (table), which the patient lies down on. 302 illustrates the first field of view from the first set of photons, which is large (covering the entirety of the torso of the patient 300). In the preferred embodiment, this would be lower dose (as compared to the second set of photons). 303 illustrates the second field of view from the second set of photons, which is medium sized (covering only a portion of the torso of the patient 300). In the preferred embodiment, this would be higher dose (as compared to the first set of photons). 304 illustrates the second field of view from the third set of photons, which is small sized (covering only a portion of the torso of the patient 300). In the preferred embodiment, this would be higher dose (as compared to the both the first set of photons and the second set of photons). This "tri-beam" fluoroscopy could be performed by multiple x-ray tubes, or, alternatively, the dynamic, variable material collimator, as described later in this patent.

Figure 4A:
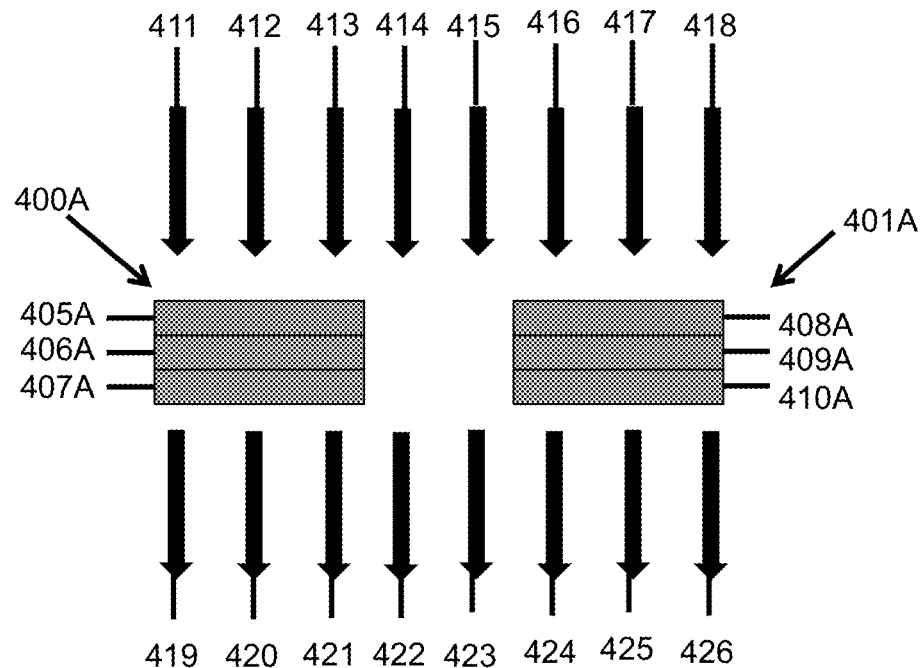
FIG. 4A illustrates a dynamic multi-layer collimator at a first configuration.

FIG. 4A illustrates a dynamic multi-layer collimator at a first configuration. 400A illustrates a first side of the collimator. 401A illustrates a second side of the collimator. 405A illustrates a first layer of the first side of the collimator 400. 406A illustrates a second layer of the first side of the collimator 400. 407A illustrates a third layer of the first side of the collimator 400. 408A illustrates a first layer of the second side of the collimator 401. 409A illustrates a second layer of the second side of the collimator 401. 410A illustrates a third layer of the second side of the collimator 401. 411 illustrates a first set of x-ray photons passing from the x-ray tube (x-ray tube not shown), which is headed towards the first side of the collimator 400A. 412 illustrates a second set of x-ray photons passing from the x-ray tube (x-ray tube not shown), which is headed towards the first side of the collimator 400A. 413 illustrates a third set of x-ray photons passing from the x-ray tube (x-ray tube not shown), which is headed towards the first side of the collimator 400A. 414 illustrates a fourth set of x-ray photons passing from the x-ray tube (x-ray tube not shown), which is headed towards the opening in the collimator 400A. 415 illustrates a fifth set of x-ray photons passing from the x-ray tube (x-ray tube not shown), which is headed towards the opening in the collimator. 416 illustrates a sixth set of x-ray photons passing from the x-ray tube (x-ray tube not shown), which is headed towards the second side of the collimator 401A. 417 illustrates a seventh set of x-ray photons passing from the x-ray tube (x-ray tube not shown), which is headed towards the second side of the collimator 401A. 418 illustrates a eighth set of x-ray photons passing from the x-ray tube (x-ray tube not shown), which is headed towards the second side of the collimator 401A. 419 illustrates the first set of x-ray photons at a later time point, which are attenuated by the first layer 405, the second layer 406 and the third layer 407. 420 illustrates the second set of x-ray photons at a later time point, which are attenuated by the first layer 405, the second layer 406 and the third layer 407. 421 illustrates the third set of x-ray photons at a later time point, which are attenuated by the first layer 405, the second layer 406 and the third layer 407. 422 illustrates the fourth set of x-ray photons at a later time point, which are not attenuated by the collimator because they pass through the opening. 423 illustrates the fifth set of x-ray photons at a later time point, which are not attenuated by the collimator because they pass through the opening. 424 illustrates the sixth set of x-ray photons at a later time point, which are attenuated by the first layer 408, the second layer 409 and the third layer 410. 425 illustrates the seventh set of x-ray photons at a later time point, which are attenuated by the first layer 408, the second layer 409 and the third layer 410. 426 illustrates the eighth set of x-ray photons at a later time point, which are attenuated by the first layer 408, the second layer 409 and the third layer 410.

Figure 4B:
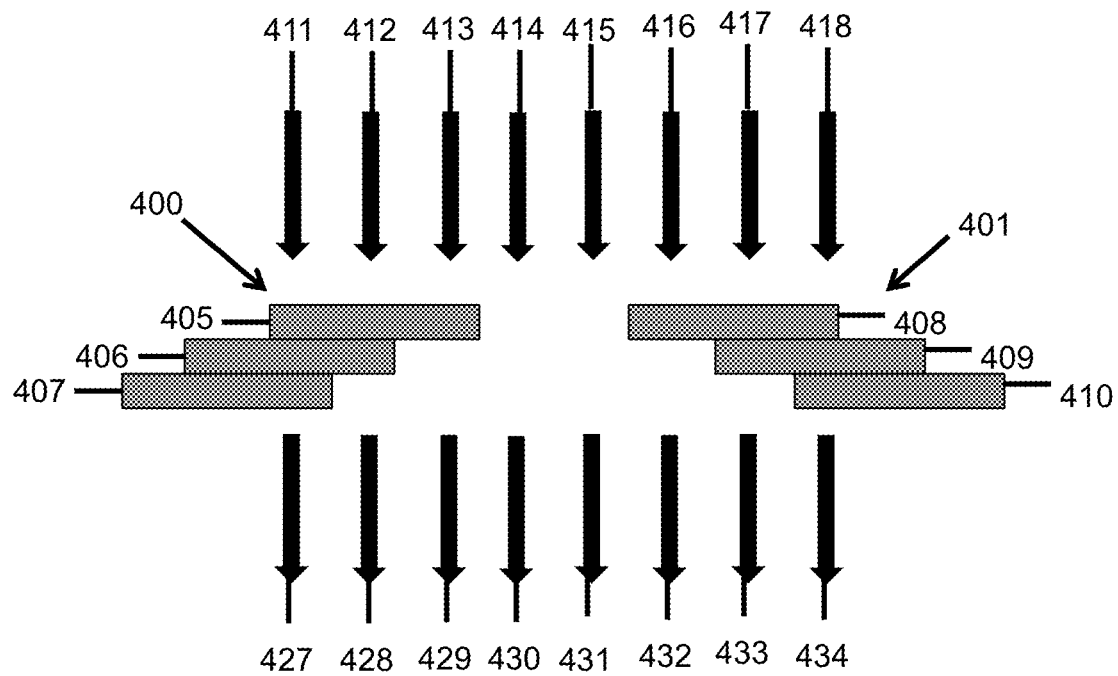
FIG. 4B illustrates a dynamic multi-layer collimator at a second configuration.

FIG. 4B illustrates a dynamic multi-layer collimator at a second configuration. 400B illustrates a first side of the collimator. Note that the layers of the first side of the collimator 400B have changed (as compared to FIG. 4A). 401B illustrates a second side of the collimator. Note that the layers of the second side of the collimator 401B have changed (as compared to FIG. 4A). 405B illustrates a first layer of the first side of the collimator 400B. 406B illustrates a second layer of the first side of the collimator 400B. 407B illustrates a third layer of the first side of the collimator 400B. 408B illustrates a first layer of the second side of the collimator 401B. 409B illustrates a second layer of the second side of the collimator 401B. 410B illustrates a third layer of the second side of the collimator 401B. 411 illustrates a first set of x-ray photons passing from the x-ray tube (x-ray tube not shown), which is headed towards the first side of the collimator 400B. 412 illustrates a second set of x-ray photons passing from the x-ray tube (x-ray tube not shown), which is headed towards the first side of the collimator 400B. 413 illustrates a third set of x-ray photons passing from the x-ray tube (x-ray tube not shown), which is headed towards the first side of the collimator 400B. 414 illustrates a fourth set of x-ray photons passing from the x-ray tube (x-ray tube not shown), which is headed towards the opening in the collimator. 415 illustrates a fifth set of x-ray photons passing from the x-ray tube (x-ray tube not shown), which is headed towards the opening in the collimator. 416 illustrates a sixth set of x-ray photons passing from the x-ray tube (x-ray tube not shown), which is headed towards the second side of the collimator 401B. 417 illustrates a seventh set of x-ray photons passing from the x-ray tube (x-ray tube not shown), which is headed towards the second side of the collimator 401B. 418 illustrates a eighth set of x-ray photons passing from the x-ray tube (x-ray tube not shown), which is headed towards the second side of the collimator 401B. 427 illustrates the first set of x-ray photons at a later time point, which are attenuated by the first layer 405, the second layer 406 and the third layer 407. 428 illustrates the second set of x-ray photons at a later time point, which are attenuated by the first layer 405 and the second layer 406. 429 illustrates the third set of x-ray photons at a later time point, which are attenuated by the first layer 405 only. 430 illustrates the fourth set of x-ray photons at a later time point, which are not attenuated by the collimator because they pass through the opening. 431 illustrates the fifth set of x-ray photons at a later time point, which are not attenuated by the collimator because they pass through the opening. 432 illustrates the sixth set of x-ray photons at a later time point, which are attenuated by the first layer 408 only. 433 illustrates the seventh set of x-ray photons at a later time point, which are attenuated by the first layer 408 and the second layer 409. 434 illustrates the eighth set of x-ray photons at a later time point, which are attenuated by the first layer 408, the second layer 409 and the third layer 410. This collimator causes a first portion of the x-ray beam (including the fourth set of x-ray photons 414 and the fifth set of x-ray photons 415) to not undergo collimator attenuation and be optimized for a first anatomic structure. This collimator causes a second portion of the x-ray beam (including the third set of x-ray photons 413 and the sixth set of x-ray photons 416) to undergo attenuation by one layer of the collimator (including layer 405 and layer 408), which will be optimized for a second anatomic structure. This collimator causes a third portion of the x-ray beam (including the second set of x-ray photons 412 and the seventh set of x-ray photons 417) to undergo attenuation by two layers of the collimator (including layers 405, 406, 408 and 409), which will be optimized for a third anatomic structure. This collimator causes a fourth portion of the x-ray beam (including the first set of x-ray photons 411 and the eighth set of x-ray photons 418) to undergo attenuation by three layers of the collimator (including layers 405, 406, 407, 408, and 409), which will be optimized for a third anatomic structure.

FIG. 5 illustrates a process for performing an optimized x-ray beam. This process improves upon the current process by optimizing the x-ray beam for each structure within the field of view. 500 illustrates the step of determining which anatomic structures (e.g., vasculature) are needed to be optimized within the field of view. 501 illustrates the step of determining the collimator setting (e.g., number of layers, type of materials, position of each collimator layer) for each anatomic structure within the field of view. 502 illustrates the step of positioning the collimator setting (e.g., number of layers, type of materials, position of each collimator layer) for each anatomic structure within the field of view. 503 illustrates the step of generating x-rays. 504 illustrates the step of adjusting the collimator settings.

FIG. 6 illustrates a process for performing an optimized x-ray beam. Traditionally, x-ray beams pass a similar set of x-rays through all tissues in the field of view. This process improves upon the current process by optimizing the x-ray beam for each structure within the field of view. 600 illustrates obtaining a low dose x-ray to determine the type and thickness of the materials within the field of view. 601 illustrates the steps of: determining the x-ray settings (kVp, mA, sec) and collimator settings for a first structure within the field of view; and, determining the x-ray settings (kVp, mA, sec) and collimator settings for at least one additional structure within the field of view. 602 illustrates performing a first image with the x-ray settings (kVp, mA, sec) and collimator settings for the first structure within the field of view. 603 illustrates performing at least one additional image with the x-ray settings (kVp, mA, sec) and collimator settings for the at least one additional structure within the field of view. 604 illustrates fusing the images. Note that the fused image will have each portion of the image optimized (e.g., region of a chest x-ray that has lungs is optimized for lungs, region of the chest x-ray that has liver is optimized for liver, etc.)

Figure 7A:
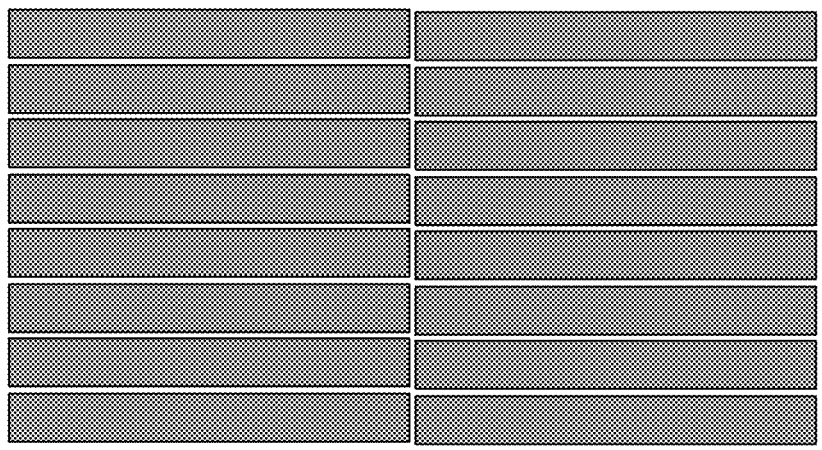
FIG. 7A illustrates the modular, multi-layered, multi-material, dynamic collimator with a first setting.

FIG. 7A illustrates the modular, multi-layered, multi-material, dynamic collimator with a first setting. Note that the collimator is made of 8 pieces on the first side 700A and eight pieces on the second side 701A. Note that they pieces are nearly touching each, so that the collimator is in a closed position. A top down view is shown.

Figure 7B:
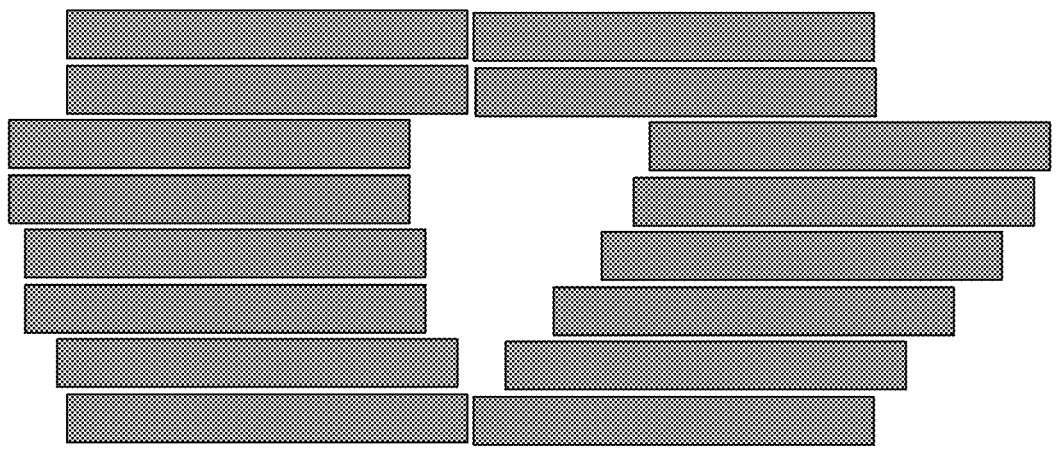
FIG. 7B illustrates the modular, multi-layered, multi-material, dynamic collimator with a second setting.

FIG. 7B illustrates the modular, multi-layered, multi-material, dynamic collimator with a second setting. Note that the collimator is made of 8 pieces on the first side 700B and eight pieces on the second side 701B. Note that they pieces have opened. The opening is designed so as to optimize the x-ray beam. For example, numerous lateral fluoroscopic images of the head could be performed during an angiogram. Note that the eyes are vulnerable to radiation. This would allow optimizing collimation to reduce dose to a specific segmented structure of the body (e.g., the eyes).

FIG. 8A illustrates a collimator made of three different materials. 800 illustrates a first material for a first side of the collimator, which is a first material (e.g., lead). 801 illustrates a second material for a first side of the collimator, which is a second material (e.g., aluminum). 802 illustrates a second material for a first side of the collimator, which is a third material (e.g., tungsten). 803 illustrates a first material for a second side of the collimator, which is a first material (e.g., lead). 804 illustrates a second material for a second side of the collimator, which is a second material (e.g., aluminum). 805 illustrates a second material for a second side of the collimator, which is third material (e.g., tungsten). The dynamic multi-layer collimator enables dividing the beam into several strengths of varying shape dynamically over time. This yields improved quality and reduced dose.

FIG. 8B illustrates a chart showing various collimator design features. Examples include: variable collimator thickness (thickness can vary); variable material (e.g., metals such as lead, steel, aluminum or non-lead materials, such as water, plastics, etc.); variable direction of placement (front, back, left right); variable speed (hollow, disk shaped collimator could be placed); variable shape of openings (e.g., opening conforms to liver, preventing radiation from contacting eyes, genitals, etc.).

FIG. 9A illustrates a process wherein the x-ray photons travel towards the detector in a parallel fashion and reach the detector in an orthogonal manner. 900 illustrates the step of produce diverging x-rays from an x-ray tube. 901 illustrates the step of using a system, which redirects diverging x-ray photons into a parallel fashion. A single or combination of curved mirror(s) or lenses can be utilized to accomplish this step. This is further described in U.S. Pat. No. 10,034,640, SPATIAL RESOLUTION IN MOLECULAR AND RADIOLOGICAL IMAGING, which is incorporated by reference. 902 illustrates the step of receive parallel x-rays at the x-ray detector in a parallel fashion.

FIG. 9B illustrates an apparatus to achieve the process as described in FIG. 9A. 903 illustrates the x-ray tube. 904 illustrates an apparatus that redirects diverging x-rays into a parallel beam directed towards the collimator. 905 illustrates a first diverging x-ray. 906 illustrates a second diverging x-ray. 907 illustrates the first diverging x-ray photon, which is directed via the redirecting apparatus 904 towards the detector 909 in a manner wherein it will pass through the patient 910 and impact the detector 909 in an orthogonal fashion (perpendicular to the detector 909). 908 illustrates a second diverging x-ray photon, which is directed via the redirecting apparatus 904 towards the detector 909 in a manner wherein it will pass through the patient 910 and impact the detector 909 in an orthogonal fashion (perpendicular to the detector 909). This process improves the existing x-ray technique because it eliminates magnification error. A first item 911 is located inside the patient 910 at a location far away from the detector 909. A second item 912 is located inside the patient 910 at a location close to the detector. Note that under these conditions the first item 911 will appear the same size as a second item 912 and will not be magnified. This process improves upon the prior art because it reduces magnification error associated with diverging x-rays.

Figure 10A:
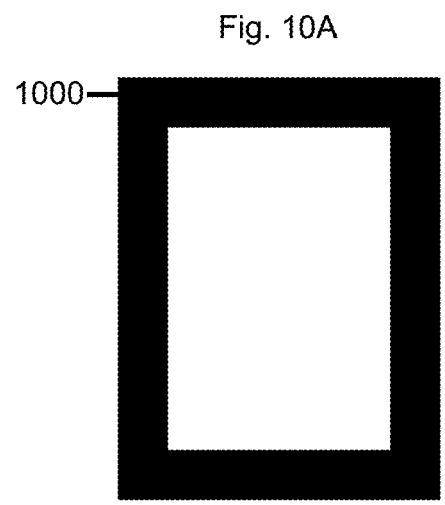
FIG. 10A illustrates a first collimator apparatus setting.

FIG. 10A illustrates a first collimator apparatus setting. 1000 illustrates a first collimator component (e.g., made of lead).

Figure 10B:
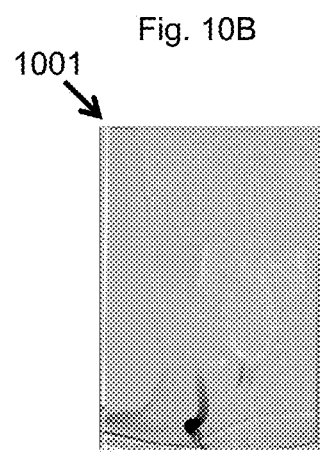
FIG. 10B illustrates a first angiogram image, which corresponds to the first collimator apparatus setting.

FIG. 10B illustrates a first angiogram image, which corresponds to the first collimator apparatus setting. 1001 illustrates a first x-ray (e.g., fluoroscopic image) showing a large field of view. Note that the area of interest is the carotid artery and this comprises only a small portion of the field of view.

Figure 10C:
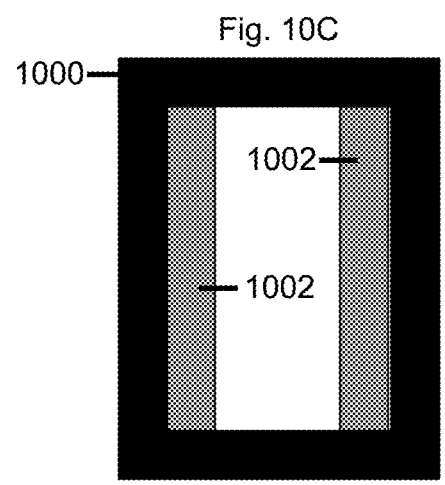
FIG. 10C illustrates a second collimator apparatus setting wherein two different material collimators are utilized for the purpose of delivering an x-ray (e.g., fluoroscopic) image where a first portion is optimized for a first anatomic feature and a second portion is optimized for a second anatomic feature.

FIG. 10C illustrates a second collimator apparatus setting wherein two different material collimators are utilized for the purpose of delivering an x-ray (e.g., fluoroscopic) image where a first portion is optimized for a first anatomic feature and a second portion is optimized for a second anatomic feature. 1000 illustrates a first collimator component (e.g., made of lead). 1002 illustrates a second collimator component (e.g., made of tungsten). This narrows the opening.

Figure 10D:
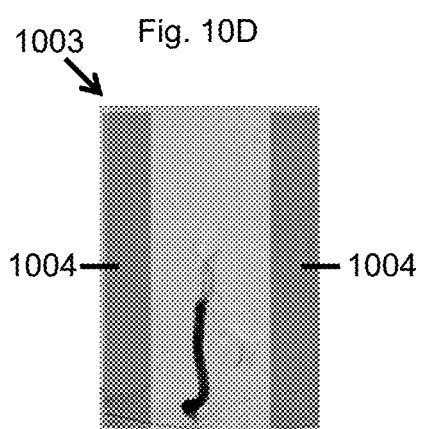
FIG. 10D illustrates a second angiogram image, which corresponds to the second collimator apparatus setting wherein both the first anatomic feature and the second anatomic feature are optimized.

FIG. 10D illustrates a second angiogram image, which corresponds to the second collimator apparatus setting wherein both the first anatomic feature and the second anatomic feature are optimized. 1003 illustrates the second angiogram image. Note that the sides 104 of the image are lower dose (less photons arrive in this region) due to the additional collimator components 1002. This improves over the prior art by reducing the dose, but also allowing some context to be visualized in the field of view.

Figure 10E:
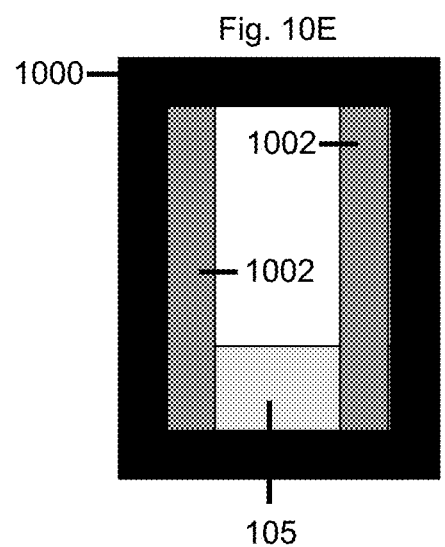
FIG. 10E illustrates a third collimator apparatus setting wherein three different material collimators are utilized for the purpose of delivering an x-ray (e.g., fluoroscopic) image where a first portion of the collimator apparatus is optimized for a first anatomic feature, a second portion of the collimator apparatus is optimized for a second anatomic feature and a third portion of the collimator apparatus is optimized for a third anatomic feature.
Figure 10F:
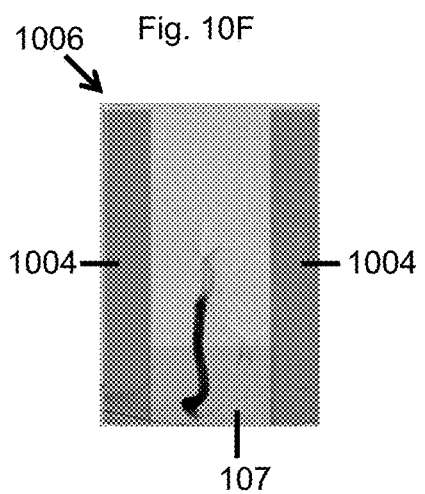
FIG. 10F illustrates a third collimator setting wherein the first anatomic feature, the second anatomic feature and the third anatomic feature are optimized.

FIG. 10E illustrates a third collimator apparatus setting wherein three different material collimators are utilized for the purpose of delivering an x-ray (e.g., fluoroscopic) image where a first portion of the collimator apparatus is optimized for a first anatomic feature, a second portion of the collimator apparatus is optimized for a second anatomic feature and a third portion of the collimator apparatus is optimized for a third anatomic feature. 1000 illustrates a first collimator component (e.g., made of lead). 1002 illustrates a second collimator component (e.g., made of tungsten). This narrows the opening. 1005 illustrates a third collimator component (e.g., made of aluminum). This narrows the opening further. FIG. 1F illustrates a third collimator setting wherein the first anatomic feature, the second anatomic feature and the third anatomic feature are optimized. 1006 illustrates the second angiogram image. Note that the sides 1004 of the image are lower dose (less photons arrive in this region) due to the additional collimator components 1002. Note that the bottom 1007 of the image is also of lower dose (less photons arrive in this region) due to the additional collimator component 1005. This improves over the prior art by reducing the dose, but also allowing some context to be visualized in the field of view.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. A method of improving image quality comprising:
   determining a first set of x-ray settings that would optimize contrast of a first set of anatomic structures;
   determining a second set of x-ray settings that would optimize contrast of a second set of anatomic structures;
   wherein said first set of x-ray settings is different from said second set of x-ray settings;
   wherein said first set of x-ray settings comprise a power, strength, and quantity of x-rays are set to optimize a large field of view and the second set of settings comprise increasing the power, strength, and quantity of x-rays to optimize a smaller field of view with improved contrast resolution;
   wherein said second set of anatomic structures comprises only a portion of said first set of anatomic structures;
   performing a first x-ray image of the first set of anatomic structures;
   performing a second x-ray image of the second set of anatomic structures; and
   fusing the first x-ray image of the first set of anatomic structures and the second x-ray image of the second set of anatomic structures to generate an optimized image wherein said second x-ray image is superimposed on said first x-ray image.

2. The method of claim 1 further comprising utilizing a first x-ray tube produces the x-rays for the first x-ray image and a second x-ray tube produces the x-rays for the second x-ray image.

3. The method of claim 2 further comprising wherein the first x-ray tube produces an x-ray beam with a wider field of view than an x-ray beam produced by the second x-ray tube.

4. The method of claim 3 further comprising wherein the first x-ray beam and the second x-ray beam overlap on a detector.

5. The method of claim 1 further comprising utilizing a collimator apparatus wherein the collimator apparatus has a first configuration to cause a first modification of the x-rays generated from an x-ray tube during the first x-ray image and a second configuration to cause a second modification of the x-rays generated from the x-ray tube during the second x-ray image.

6. The method of claim 5 further comprising wherein the collimator apparatus comprises at least two types of materials.

7. The method of claim 5 further comprising wherein the collimator apparatus comprises at least two levels of thickness.

8. The method of claim 5 further comprising wherein the collimator apparatus adjusts its position based on eye tracking data.

9. The method of claim 5 further comprising wherein the collimator apparatus adjusts its position based on inputs from an artificial intelligence system.

10. The method of claim 5 further comprising wherein the collimator apparatus has a modular construction to be able to form complex shapes to match that of a segmented structure within a patient.

11. The method of claim 5 further comprising wherein the first x-ray image is taken at a first time point and the second x-ray image is taken at a second time point.

12. The method of claim 5 further comprising wherein the first set of x-ray settings comprising mA during the first x-ray image is different from the second set of x-ray settings comprising mA during the second x-ray image.

13. The method of claim 5 further comprising wherein the first set of x-ray settings comprising kVp during the first x-ray image is different from the second set of x-ray settings comprising kVp during the second x-ray image.

14. The method of claim 5 further comprising performing fluoroscopic images.

15. The method of claim 1 further comprising wherein x-ray photons reach a detector in an orthogonal fashion.

16. The method of claim 15 further comprising wherein the detector a flat panel detector.

17. The method of claim 16 further comprising wherein the flat panel detector a measures at least 50 cm in at least one dimension.

18. The method of claim 1 further comprising:
  determining at least one additional set of x-ray settings that would optimize contrast of at least one additional set of anatomic structures; and
  performing the at least one additional x-ray image of at the least one additional set of anatomic structures; and
  fusing the at least one additional x-ray image to the optimized image.

19. The method of claim 1 further comprising utilizing a curved detector.

* * * * *